Figure 1:
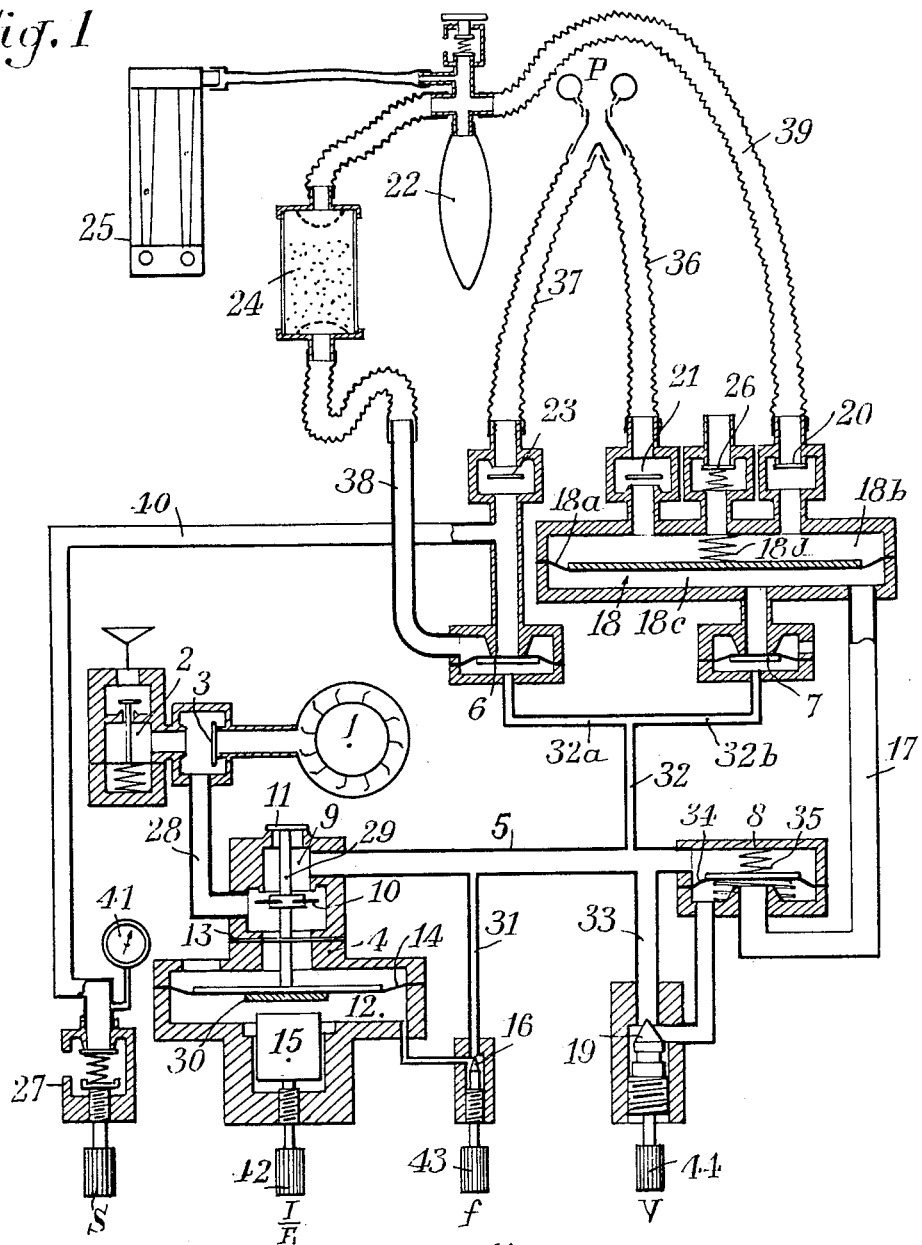

United States Patent [19]

Metivier

[11] 4,056,099
[45] Nov. 1, 1977

[54] VOLUMETRIC RESPIRATION EQUIPMENT

[76] Inventor: Robert Metivier, 49 rue du Docteur Blanche, 75016 Paris, France

[21] Appl. No.: 650,610

[22] Filed: Jan. 20, 1976

[30] Foreign Application Priority Data

Jan. 20, 1975 France .............................. 75.01615

[51] Int. Cl.[2] .......................................... A61M 16/00
[52] U.S. Cl. ................................................ 128/145.6
[58] Field of Search .............. 128/145.8, 145.6, 145.5, 128/142, 142.2, 188; 137/524.14

[56] References Cited

U.S. PATENT DOCUMENTS

| 2,121,311 | 6/1938 | Anderson et al. | 128/145.8 |
| 3,467,092 | 9/1969 | Bird et al. | 128/145.6 |
| 3,515,133 | 6/1970 | Parker | 128/142.2 |
| 3,527,213 | 9/1970 | Schreiber | 128/188 |
| 3,530,856 | 9/1970 | Bird et al. | 128/145.6 |
| 3,537,450 | 11/1970 | Fox | 128/145.6 |
| 3,604,415 | 9/1971 | Hoenig | 128/145.8 |
| 3,662,751 | 5/1972 | Barkalow et al. | 128/145.8 |
| 3,814,091 | 6/1974 | Henkin | 128/145.5 |
| 3,840,006 | 10/1974 | Buck et al. | 128/145.8 |
| Re. 25,871 | 10/1965 | Andreasen | 128/145.8 |

Primary Examiner—Robert W. Michell
Assistant Examiner—Henry J. Recla

[57] ABSTRACT

This volumetric respiration equipment is of the type comprising means for spraying air, oxygen and/or anesthetic products into the patient's lungs and to produce alternatively a negative pressure therein, said means incorporating a source of fluids under pressure as well as a circuit for said fluids, and being associated with respiratory valves and also with means for operating the equipment with the maximum reliability. Said source of fluids under pressure is such that it can deliver the fluids into the circuit under a pressure relatively low yet higher than the pressure that the patient's lungs can normally withstand, the proportioning of the inhaling to breathing-out cycle periods being obtained without resorting to any electric circuit, but only by using the motive power derived from the pressure fluid supply.

4 Claims, 2 Drawing Figures

U.S. Patent     Nov. 1, 1977     4,056,099

VOLUMETRIC RESPIRATION EQUIPMENT

The present invention relates in general to volumetric respiration equipment and has specific reference to an apparatus adapted to spray a constant volume of gaseous fluid, irrespective of the lung resistance of the patient, especially for long-term servo-action anesthesias and reanimations.

Electrical reanimation and/or anesthesia equipment of the servo-action respiration type have been known for many years; this equipment comprises respiratory valves and a device capable of alternatively blowing or spraying air, oxygen or anesthetic substances into the patient's lungs and producing a negative pressure therein. Each valve is associated with a photocell controlling the operation of the means incorporated by the equipment for producing the servo-action reanimation or anesthesia of the patient. As a rule, this equipment operates under pressures of the order of 1 to 3 bars.

Other equipment of this type which is known in the art operates likewise with pressures of this order of magnitude.

Now a pressure of 100 grams per sq.cm. in the lungs is sufficient. A first feature of the respiration equipment according to this invention is that its supply pressure is of the order of 120 g/sq.cm.. Thus, the following advantages are obtained:

the noise, rather unpleasant to the patient, is reduced considerably by using a low-pressure compressor;

the risks of over-pressure are reduced appreciably, and the gas consumption is also reduced On the other hand, the use of a low-pressure equipment permits of spraying into the patient's lung a gas having a temperature of up to 30° C. Under pressures of the order of 2 bars, the gas is relatively cold, and this may be a source of discomfort for the patient.

The air or oxygen under pressure (of the order of 120 g/sq. cm) may be supplied by using an annular compressor, or a compressed-gas cylinder (air or oxygen) provided with a suitable pressure-reducing device, through the pipe line equipping the hospital buildings.

Now humidity may interfere with the operation of equipment according to the prior art incorporating pneumatic delay-action means. This inconvenience is avoided with the respiration equipment according to this invention.

Another feature characterizing the apparatus according to the present invention is that the pattern of the inhaling breathing-out cycle is controlled not by an electric circuit but by the motive power derived from the supply fluid under pressure.

Figure 2:
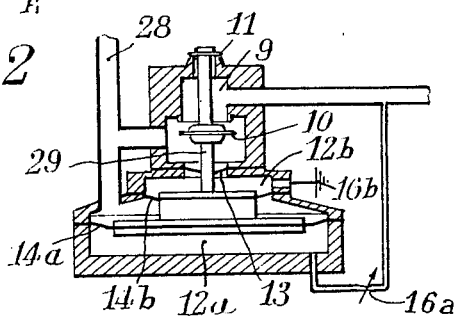

A typical form of embodiment of the present invention will now be described by way of illustration with reference to the accompanying drawing, in which:

FIG. 1 is a diagrammatic general view of the equipment of this invention, designed for performing a servo-action anesthesia, and FIG. 2 illustrates a modified form of embodiment of the component element of the equipment of FIG. 1 which is intended for producing a predetermined inhaling breathing-out ratio.

The respiration equipment for servo-action anesthesia which is illustrated in FIG. 1 of the drawing is fed either with gas delivered from the output port of an annular compressor 1 at the rate of 200 liters/mn, and under a stable pressure of 120 g/sq.cm., or with gas received from a compressed-gas cylinder and having its pressure reduced and restored to a value equivalent to that obtained through the compressor 1, by using a pressure-reducing device 2 of suitable type. When the compressor 1 is operated, the valve member 3 is actuated and shuts the outlet of pressure-reducing device 2. Conversely, during the operation of the pressure-reducing device 2, the valve member 3 closes the outlet of compressor 1.

The supply assembly is connected via a pipe line 28 to another assembly 4 comprising two chambers, namely:

a first chamber 9 separated from the external atmosphere on one side by the membrane 13 and on the other side by a valve member 11, said chamber 9 being provided in its central portion with a valve member 10 adapted to permit or prevent the circulation of gas through a pipe line 5. These valve members 10 and 11 are rigidly interconnected by means of a rod 29 so that closing the valve member 11 will open automatically the other valve member 10, and vice-versa;

another chamber 12 isolated from the surrounding atmosphere by a membrane 14 rigidly connected through said rod 29 to both valve members 10 and 11. Enclosed in this chamber 12 is a permanent magnet 15 of which the position is controlled by a screw provided with a knob 42 for adjusting the inhaling to breathing-out ratio I/E.

A soft-iron plate 30 secured to said membrane 14 is responsive to the magnetic field of magnet 15. Chamber 12 communicates via a branch line 31 with pipe line 5. The amount of gas allowed to penetrate into this chamber 12 is adjusted by means of a needle valve 16 controlled in turn by means of a screw rigid with the knob 43 for adjusting the frequency $f$.

The pipe line 5 comprises two branch lines, namely:

branch line 32 having its outlets 32a and 32b opening into a pair of diaphragm-valves 6 and 7, respectively;

branch line 33 supplying the output regulator 8; the volume V of the output thus controlled is adjustable by means of knob 44 rigid with a screw having a needle-valve forming end portion 19. The function of this regulator is to compensate the patient's reactions, in other words the different values assumed by the lung resistances or compliances of the patient P. As the patient's reaction increases, the membrane 34 is urged upwards and thus tends to compress the spring 35 to provide a constant output through pipe line 17, the pressure in pipe line 5 being constant.

The gas from pipe line 17 flows into a chamber 18 divided by a membrane 18a into an upper chamber 18b and a lower chamber 18c. This membrane 18a is compensated by a return spring 18d.

The lower chamber 18c is isolated from the external or surrounding atmosphere by the membrane of valve 7 and the upper chamber 18b communicates with the bladder 22 of the generator supplying the gases necessary for the patient's respiration with the interposition of a valve 20, said gas mixture flowing through valve 21 and pipe line 36 into the patient's lungs; moreover, a gauged valve 26 enables the patient, in case of failure in any gas output, to breathe atmospheric air.

The gas breathed out by the patient flows through the hose 37, valves 23 and 6, and pipe line 38 and penetrates into the box 24 filled with soda lime for fixing the carbon monoxide; then, it flows into the bladder 22 from which it is eventually recycled via a hose 39 in the aforementioned upper chamber 18b.

The rotameter 25 connected to said bladder 22 delivers a continuous supply of anesthetic gases and oxygen as required for the patient's anesthesia.

The equipment illustrated in the drawing further comprises a safety valve 27 adjustable by means of another knob S and connected to the pipe line 40 interconnecting the valves 23 and 6. A pressure gauge 41 displays continuously the respiratory pressure.

Alternatively, the assembly 4 may comprise as illustrated in FIG. 2 on the one hand a chamber 9 similar to the one shown in FIG. 1 and incorporating a pair of valves 11 and 10, this chamber 9 being separated from the atmosphere by a membrane 13, and on the other hand a chamber 12a separated from the inlet pipe line 28 by a membrane 14a. The outlet of this pipe line 28 is closed by the membrane 14b. Both valves 10, 11 and the membranes 13, 14b and 14a are operatively interconnected by the axial rod 29. Between membranes 13 and 14b a chamber 12b equipped with an adjustable valve 16b is disposed.

In this modified assembly the ratio I/E is subordinate to the difference between the surface areas of membranes 14a and 14b, and can be adjusted by means of the spring-loaded valve 16b. The frequency regulation is performed as in the preceding case by means of a valve 16a of same type as valve 16.

The device of this invention operates as follows:

The source of gas under pressure is connected to the supply circuit, or the compressor 1 is operated; in the initial position, the magnet 15 attracts the soft iron plate 30 underlying the membrane 14. Thus, this membrane 14 is urged downwardly and valve 11 isolates chamber 9 from the atmosphere, valve 10 being opened to permit the flow of gas into chamber 9 via pipe line 5, thus closing the valve members rigid with membranes 6 and 7 for supplying the output regulator 8.

The volume of gas in pipe line 5 is adjusted by means of valve 19 and output regulator 8, and this gas flows through line 17 to fill the lower chamber 18c. The gas pressure actuates the membrane 18d, thus forcing the content of the upper chamber 18d into the patient's lung via the valve member 21 unseated by the gas pressure.

This constitutes the inhaling period.

However, the gas filling the pipe line 5 is throttled by the adjusted needle valve 16. Chamber 12 is thus filled until the pressure produces a force capable of overcoming the force of magnet 15. Thus, membrane 14 is pushed back to close valve 10 and thus prevent the gas received from the compressor or compressed-gas cylinder from penetrating into chamber 9 while opening the valve 11 and connecting the aforesaid pipe line 5 to the atmosphere. Thus, chamber 12 is exhausted via needle valve 16, pipe line 5 and open valve 11. The magnet 15 attracts again the membrane 14, and the cycle may start again for another spray into the patient's lungs.

However, during the exhaust period of pipe line 5 and chamber 9, i.e., during the breathing-out period, both valves 6 and 7 are open; thus:

since valve 7 is open, the output regulator 8 is restored to atmospheric pressure, this also applying to pipe line 17 and lower chamber 18c; the membrane 18a falls back and valve member 20 opens, thus inhaling the gases contained in bladder 22 of the gas generator, and filling the upper chamber 18b since valve 21 was reclosed as a consequence of the negative pressure created in said upper chamber 18b. On the other hand, opening the valve 7 will also drain the driving gas out from pipe line 17 via the lower chamber 18c;

since valve 6 is open, the patient can breath out through valve 23 and the outgoing gas flows through pipe line 38 communicating with hose 37, so as to be recycled as already explained in the foregoing.

Stopping the output of gases necessary for the patient creates a negative pressure in the upper chamber 18b; thus, the gauged valve 26 is operated and the patient can breath atmospheric air directly.

From the above description it will be seen that the following adjustments can be made during the operation of this volumetric respiration equipment:

adjustment of the volume of gas per minute by means of valve 19 upstream of chamber 18. As a rule, a respiration apparatus of this type is operated at the rate of 100 liters per minute;

adjustment of the breathing frequency by means of the needle valve 16. This frequency may range from 6 to 60 cycles per minute;

adjustment of the inhalating time to breathing-out time ratio I/E by moving the magnet 15 forwards or backwards so as to attract more or less the soft iron plate 30 and the membrane 14 rigid therewith. In fact, the inhaling time of the apparatus according to the invention corresponds to the time necessary for filling the chamber 12 until the assembly 14, 11 and 10 and is released to open the valve 11 and close the valve 10 when the membrane 14 is outside the range of magnetic attraction of the magnet 15; the draining time of this chamber 12 determines the breathing-out time. This ratio I/E may vary from (1/1.5) to (1/4). As a rule, a ratio of (1/2) will be adequate;

adjustment of the breathing pressure readable on the dial of the pressure gauge 41 and maintained by the gauged valve 26 at a value between 30 and 100 g/sq.cm.

The above-described mode of operation of the apparatus according to this invention refers to an anesthesia under servo-action respiration conditions.

It may be noted that this equipment may be used for a closed-circuit spontaneous respiration anesthesia; in this case, the respiration apparatus proper is stopped and the gas circuit is a follows: bladder 22, hose 39, chamber 18b, hoses 36, 37 and 38, and soda-lime box 24. This apparatus may also be used for reanimation or rescue purposes with atmospheric air, with or without oxygen supply.

In the case corresponding to the ventilation of a patient with atmospheric air, the apparatus is disconnected from the gas generator and the patient will breathe out directly to the atmosphere through valve 6.

Of course, the above-described form of embodiment of the invention, as well as the modifications proposed, described or suggested herein, with reference to the attached drawing, should not be construed as limiting the scope of the invention since various other modifications and changes may be brought thereto without departing from the basic principles of the invention as set forth in the appended claims.

What I claim is:

1. Volumetric respirator for reanimating a patient, comprising, in combination:
   a source of gases necessary for the patient's respiration;
   control means for inhalating said gases into the patient's lungs and subsequently permitting the patient's exhalation with an adjustable inhalation time to exhalation time ratio, said control means including a housing having first and second chambers separated by diaphragm means, an inlet valve connected to said first chamber, a first conduit connecting said source with said inlet valve, inhalation valve means connected to said first chamber adapted to open for allowing the flow of said gases into the patient's lungs, and exhalation valve means adapted to open for subsequently allowing the flow of the gas breathed out by said patient, patient connection means, a first controlled membrane-type valve member closed during the inhalation time and open during the exhalation time, said first controlled membrane-type valve member having an inlet port communicating with said second chamber, a control port and a vent port;

an inhalation gas conduit connecting said inhalation valve means with said patient connection means;

an exhalation gas conduit connecting said patient connection means with said exhalation valve means, a second controlled membrane-type valve member having an inlet port communicating with said exhalation valve means, a control port and a vent port, a second conduit connecting said vent port of said second controlled membrane-type valve member with said source, said second conduit including means permitting the regeneration of the gas breathed out by the patient;

means for preserving the safety of operation of said respirator, consisting of a safety valve communicating with said exhalation gas conduit;

means controlling said control means for inhalating said gases from said source into the patient's lungs and subsequently causing the patient to exhale comprising:

a source of control fluid under pressure;

a main circuit for directing said control fluid under pressure towards said second chamber;

a circuit branched off said main control fluid circuit, which comprises in turn two branch lines leading to the control ports of said first and second membrane-type valve members, respectively;

means permitting the delivery of said control fluid to said main circuit under a low pressure higher however than the pressure that the patient's lungs can withstand;

said means controlling said control means including a housing having first and second chambers, said first chamber including an inlet port communicating with said source of control fluid, an outlet port communicating with said second chamber and an exhaust port communicating with atmosphere, and valve means for closing said inlet port and opening said exhaust port simultaneously, and opening said exhaust port and closing said inlet port simultaneously, said second chamber including movable means operatively associated with said valve means, filling means communicating between said main circuit and said second chamber of said controlling means for filling said second chamber with control fluid during a time period corresponding to the inhalation period and to be emptied during another time period corresponding to the exhalation time, and means associated with said filling means for adjusting as required the inhalation time to exhalation time ratio;

said filling means including a needle valve for adjusting the frequency of the filling and emptying phases of said chamber in said control assembly;

means between said means controlling said control means and said second chamber capable of providing a constant control fluid output, whereby the patient's compliance is compensated, said means providing a constant control fluid output including means for adjusting the value of said output.

2. Volumetric respirator as claimed in claim 1, wherein the pressure of the control fluid delivered to the main circuit is of the order of 120 g/sq.cm.

3. Volumetric respirator for anesthesia under assisted-respiration conditions, comprising, in combination:

a source of anesthetic gases and oxygen necessary for the patient;

control means for inhalating said anesthetic gases and oxygen into the patient's lungs and subsequently permitting the patient's exhalation with an adjustable inhalation time to exhalation time ratio, said control means including a housing having first and second chambers separated by diaphragm means, an inlet valve connected to said first chamber, a first conduit connecting said source with said inlet valve, inhalation valve means connected to said first chamber adapted to open for allowing the flow of said anesthetic gases and oxygen into the patient's lungs, and exhalation valve means adapted to open for subsequently allowing the flow of the gas breathed out by said patient, patient connection means, a first controlled membrane-type valve member closed during the inhalation time and open during the exhalation time, said first controlled membrane-type valve member having an inlet port communicating with said second chamber, a control port and a vent port;

an inhalation gas conduit connecting said inhalation valve means with said patient connection means;

an exhalation gas conduit connecting said patient connection means with said exhalation valve means, a second controlled membrane-type valve member having an inlet port communicating with said exhalation valve means, a control port and a vent port, a second conduit connecting said vent port of said second controlled membrane-type valve member with said source, said second conduit including means permitting the regeneration of the gas breathed out by the patient;

means for preserving the safety of operation of said respirator, consisting of a safety valve communicating with said exhalation gas conduit;

means controlling said control means for inhalating said anesthetic gases and oxygen from said source into the patient's lungs and subsequently causing the patient to exhale comprising:

a source of control fluid under pressure;

a main circuit for directing said control fluid under pressure towards said second chamber;

a circuit branched off said main control fluid circuit, which comprises in turn two branch lines leading to the control ports of said first and second membrane-type valve members, respectively;

means permitting the delivery of said control fluid to said main circuit under a low pressure higher however then the pressure that the patient's lungs can withstand;

said means controlling said control means including a housing having first and second chambers, said first chamber including an inlet port communicating with said source of control fluid, an outlet port communicating with said second chamber and an exhaust port communicating with atmosphere, and valve means for closing said inlet port and opening said exhaust port simultaneously, and opening said exhaust port and closing said inlet port simultaneously, said second chamber including movable means operatively associated with said valve means, filling means communicating between said main circuit and said second chamber of said controlling means for filling said second chamber with control fluid during a time period corresponding to the inhalation period and to be emptied during another time period corresponding to the exhalation time, and means associated with said filling means for adjusting as required the inhalation time to exhalation time ratio;

said filling means including a needle valve for adjusting the frequency of the filling and emptying phases of said chamber in said control assembly;

means between said means controlling said control means and said second chamber capable of providing a constant control fluid output, whereby the patient's compliance is compensated, said means providing a constant control fluid output including means for adjusting the value of said output.

4. Volumetric respirator for ventilating a patient, comprising, in combination:

a source of gases necessary for the patient's respiration;

control means for inhalating said gases into the patient's lungs and subsequently permitting the patient's exhalation with an adjustable inhalation time to exhalation time ratio, said control means including a housing having first and second chambers separated by diaphragm means, an inlet valve connected to said first chamber, a first conduit connecting said source with said inlet valve, inhalation valve means connected to said first chamber adapted to open for allowing the flow of said gases into the patient's lungs, and exhalation valve means adapted to open for subsequently allowing the flow of the gas breathed out by said patient, patient connection means, a first controlled membrane-type valve member closed during the inhalation time and open during the exhalation time, said first controlled membrane-type valve member having an inlet port communicating with said second chamber, a control port and a vent port;

an inhalation gas conduit connecting said inhalation valve means with said patient connection means;

an exhalation gas conduit connecting said patient connection means with said exhalation valve means, a second controlled membrane-type valve member having an inlet port communicating with said exhalation valve means, a control port and a vent port, a second conduit connecting said vent port of said second controlled membrane-type valve member with atmosphere;

means for preserving the safety of operation of said respirator, consisting of a safety valve communicating with said exhalation gas conduit;

means controlling said control means for inhalating said gases from said source into the patient's lungs and subsequently causing the patient to exhale comprising:

a source of control fluid under pressure;

a main circuit for directing said control fluid under pressure towards said second chamber;

a circuit branched off said main control fluid circuit, which comprises in turn two branch lines leading to the control ports of said first and second membrane-type valve members, respectively;

means permitting the delivery of said control fluid to said main circuit under a low pressure higher however than the pressure that the patient's lungs can withstand;

said means controlling said control means including a housing having first and second chambers, said first chamber including an inlet port communicating with said source of control fluid, an outlet port communicating with said second chamber and an exhaust port communicating with atmosphere, and valve means for closing said inlet port and opening said exhaust port simultaneously, and opening said exhaust port and closing said inlet port simultaneously, said second chamber including movable means operatively associated with said valve means, filling means communicating between said main circuit and said second chamber of said controlling means for filling said second chamber with control fluid during a time period corresponding to the inhalation period and to be emptied during another time period corresponding to the exhalation time, and means associated with said filling means for adjusting as required the inhalation time to exhalation time ratio;

said filling means including a needle valve for adjusting the frequency of the filling and emptying phases of said chamber in said control assembly;

means between said means controlling said control means and said second chamber capable of providing a constant control fluid output, whereby the patient's compliance is compensated, said means providing a constant control fluid output including means for adjusting the value of said output.

* * * * *